United States Patent [19]

Soltys et al.

[11] Patent Number: 5,480,552

[45] Date of Patent: * Jan. 2, 1996

[54] METHOD FOR CONCENTRATING A SOLUTE WITH AN OSCILLATING FILTRATION DEVICE

[75] Inventors: Paul Soltys, Lake Zurich; Norma Ofsthun, Rolling Meadows, both of Ill.

[73] Assignee: Baxter International Inc., Deerfield, Ill.

[*] Notice: The portion of the term of this patent subsequent to Jan. 10, 2012, has been disclaimed.

[21] Appl. No.: 194,213

[22] Filed: Feb. 9, 1994

Related U.S. Application Data

[63] Continuation-in-part of Ser. No. 28,400, Mar. 9, 1993, abandoned, which is a continuation-in-part of Ser. No. 818,851, Jan. 10, 1992, Pat. No. 5,240,614.

[51] Int. Cl.$^6$ .................................................. B01D 61/28
[52] U.S. Cl. ..................................... 210/645; 210/500.23
[58] Field of Search ............................. 210/645, 500.23, 210/500.41, 644; 264/41, 209.1

[56] References Cited

U.S. PATENT DOCUMENTS

| | | |
|---|---|---|
| 4,230,463 | 10/1980 | Henis et al. . |
| 4,276,172 | 6/1981 | Henne et al. . |
| 4,286,015 | 8/1981 | Yoshida et al. . |
| 4,351,860 | 9/1982 | Yoshida et al. . |
| 4,361,484 | 11/1982 | Larsson et al. ........................ 210/632 |
| 4,610,791 | 9/1986 | Henne et al. . |
| 4,802,942 | 2/1989 | Takemura et al. . |
| 4,804,628 | 2/1989 | Cracauer ........................ 210/321.8 X |
| 4,822,489 | 4/1989 | Nohmi et al. . |
| 4,882,223 | 11/1989 | Aptel et al. . |
| 4,983,293 | 1/1991 | Yoshida et al. . |
| 5,049,276 | 9/1991 | Sasaki . |
| 5,240,614 | 8/1993 | Ofsthun et al. ........................ 210/645 |

FOREIGN PATENT DOCUMENTS

| | | |
|---|---|---|
| 60-246812 | 12/1985 | Japan . |
| 61-164602 | 7/1986 | Japan . |
| 62-117812 | 5/1987 | Japan . |

Primary Examiner—Frank Spear
Attorney, Agent, or Firm—Thomas S. Borecki; Charles R. Mattenson; Robert M. Barrett

[57] ABSTRACT

Dual-skinned membranes are provided useful as one-way or rectifying membranes which reduce back filtration of solute molecules in dialysis and which improve nutrient supply and product recovery in membrane bioreactors. The membranes are dual-skinned polymeric materials preferably in the form of hollow fibers. The membranes have skins of polymer on the opposite sides with differing permeability to solutes and sieving coefficient characteristics. The skin on each side have pores that are invisible at 10,000 times magnification. A microporous structure between the skins contains pores capable of retaining solutes in a molecular weight range of about 5000 to 200,000 in an increased concentration between the interior and the exterior skins. Improved dialysis devices are formed by using bundles of the hollow fiber membranes as a dialysis member having rectifying properties.

17 Claims, 8 Drawing Sheets

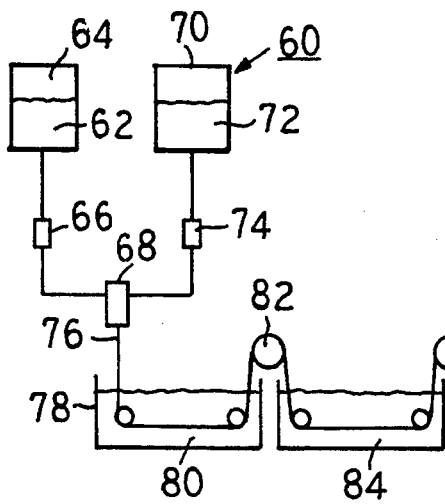
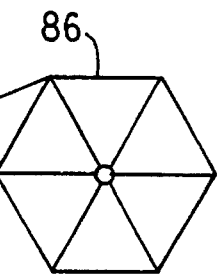
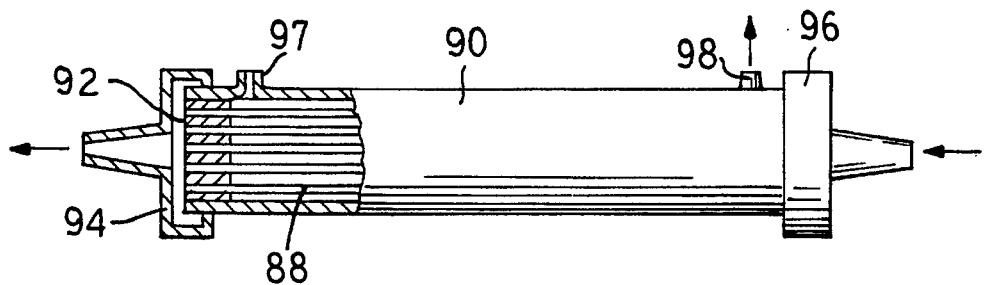
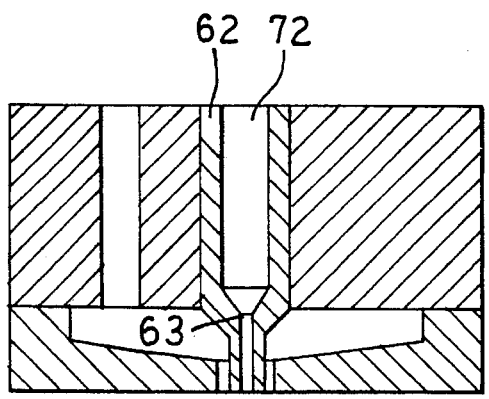
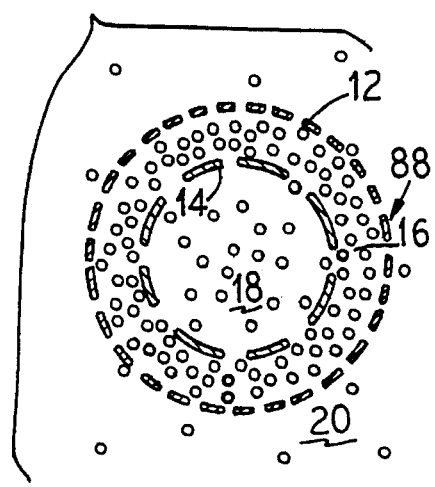
FIG. 1
FIG. 3
FIG. 2
FIG. 4

— LUMEN TO SHELL
— SHELL TO LUMEN

— LUMEN TO SHELL
— SHELL TO LUMEN

- ■ C1 END
- □ C1 MID
- ● C2 END
- ○ C2 MID

METHOD FOR CONCENTRATING A SOLUTE WITH AN OSCILLATING FILTRATION DEVICE

BACKGROUND OF THE INVENTION

This application is a continuation in part of commonly assigned, application having U.S. Ser. No. 08/028,400, filed Mar. 9, 1993, and now abandoned, which is a continuation in part of commonly assigned U.S. patent application Ser. No. 07/818,851, filed Jan. 10, 1992, now U.S. Pat. No. 5,240,614.

This invention relates generally to fluid filtration devices, such as blood dialysis devices and bioreactors and membranes for such devices. More specifically, the invention relates to an improved dialysis device having rectifying filtration properties, dual-skinned membranes for performance of such dialysis and other filtration procedures.

Dialysis membranes and devices perform important life sustaining functions when used in artificial kidneys and other types of filtration devices. A well-recognized problem of high flux dialyzers is the back filtration from dialysate to the blood of undesirable molecules. Due to the high cost of using sterile, pyrogen-free dialysates, it would be highly desirable to have available a dialysis membrane which could remove relatively large solutes such as $\beta$-2 microglobulin while preventing passage of similarly sized molecules from dialysate to blood.

However, such membranes which offer a high rate of diffusion of solutes from the blood to dialysate also suffer from high rates of back diffusion of solutes from dialysate back to the blood. Similarly, existing membranes which offer a high rate of convection also suffer from high rates of back filtration. A need has, therefore, existed for dialysis membranes which provide for adequate removal of uremic toxins from the blood while preventing back transport of undesirable substances to the blood. Similarly, other fluid filtration processes benefit from the availability of membranes having such rectifying properties.

A need has also existed for devices, such as bioreactors, in which rectifying membranes provide a means for simultaneously supplying nutrients to and carrying products and waste byproducts from live cells that are used to make products which cannot be economically produced by traditional synthetic chemistry techniques.

SUMMARY OF THE INVENTION

A method is provided by the present invention using membranes within a filtration device, such as a dialysis device. The filtration device containing the membranes has rectifying properties, i.e. an asymmetric sieving coefficient. An asymmetric sieving coefficient exists in a situation in which, for a given solute, the fraction of the solute which passes through the membrane in one direction is substantially different than the fraction of the solute which passes through the membrane in the opposite direction.

To this end, in an embodiment, a method is provided for removing unwanted material from a solution. The method comprises the steps of: providing a device having a plurality of dual-skinned hollow membranes secured in a generally parallel orientation in an enclosure, each of the plurality of membranes having a microporous structure therein providing an asymmetric sieving coefficient with respect to passage of the solution with the unwanted material; causing the solution to flow through the device a plurality of times; and removing the unwanted material from the solution as the solution is transferred through the device.

In an embodiment, the sieving coefficient is between 0.1 and 0.9 inclusive.

In an embodiment, the solution includes a dialysis fluid.

In an embodiment, the method further comprises the steps of: providing a first reservoir on one side of the membrane; and providing a second reservoir on a second side of the membrane wherein the solution is caused to flow between the first reservoir and the second reservoir through the device.

In an embodiment, the method further comprises the step of providing an inflow means in fluid communication with interiors of the membranes.

In an embodiment, the method further comprises the step of providing an outflow means in fluid communication with ends of the membranes for outflow of the solution.

In an embodiment, the method further comprises the step of providing a second fluid flow path in fluid communication with an interior of the enclosure wherein the solution can be caused to flow in contact with exterior surfaces of the membranes.

In an embodiment, the unwanted material is in a defined range of molecular weights.

In another embodiment of the present invention, a method is provided for removing unwanted material from a bodily fluid. The method comprises the steps of: providing a dialysis device having a plurality of dual-skinned polymeric membranes, each having a shell side and a lumen side and each secured at opposite ends in a generally parallel orientation within an enclosure; providing an inflow means for a liquid subjected to dialysis, the inflow means in fluid communication with the lumen sides of the membrane; providing an outflow means in fluid communication with ends of the membrane for outflow of the bodily fluid after filtration; and causing the bodily fluid to flow through the device a plurality of times wherein the unwanted material collects in or on the shell side of the membranes.

In an embodiment, the plurality of membranes have a microporous structure.

In an embodiment, the microporous structure provides an asymmetric sieving coefficient.

In another embodiment of the present invention, a method is provided for producing biological products by confining living cells in a bioreactor vessel, the vessel having a plurality of dual-skinned hollow membranes with a microporous structure having an asymmetric sieving coefficient, the membrane being secured in a generally parallel orientation in an enclosure having an interior wherein the exteriors of the membranes and the interior of the enclosure define the bioreactor vessel. The method comprises the steps of: causing a fluid containing nutrients for the cells to repeatedly flow through the hollow membranes in cycles to allow transport of the nutrients through the membrane to the cells; removing waste material from the cells as the waste materials are transferred through the membrane to the fluid; and removing a biological product from the vessel.

It is, therefore, an advantage of the present invention to provide a device to separate and concentrate a desired solute.

A further advantage of the present invention is to provide a method for separating and concentrating a desired solute by repeatedly cycling a solution back and forth across a membrane.

Yet another advantage of the present invention is to provide a method for separating and concentrating solute on one side of the membrane.

Still further, an advantage of the present invention is to provide a method for concentrating a solute on the lumen side of the membrane.

And, another advantage of the present invention is to continually increase concentration of solute using a rectifying membrane as the number of cycles increase.

A still further advantage of the present invention is to increase concentration of solute using a rectifying membrane independent of the operating conditions.

Additional features and advantages of the present invention are described in, and will be apparent from, the detailed description of the presently preferred embodiments and from the drawings.

BRIEF DESCRIPTION OF THE DRAWINGS

FIG. 1 is a diagrammatic view illustrating the process for forming membranes of the invention in hollow fiber form.

FIG. 2 is a cross-sectional view of an annular extrusion die used in the practice of the invention.

FIG. 3 is a side elevational view with portions in cross-section of a filtration device of the present invention.

FIG. 4 is a sketch in greatly enlarged scale illustrating, hypothetically, the mechanism of filtration that occurs in use of the filtration devices of the invention.

DETAILED DESCRIPTION OF THE PRESENTLY PREFERRED EMBODIMENTS

Figure 5:
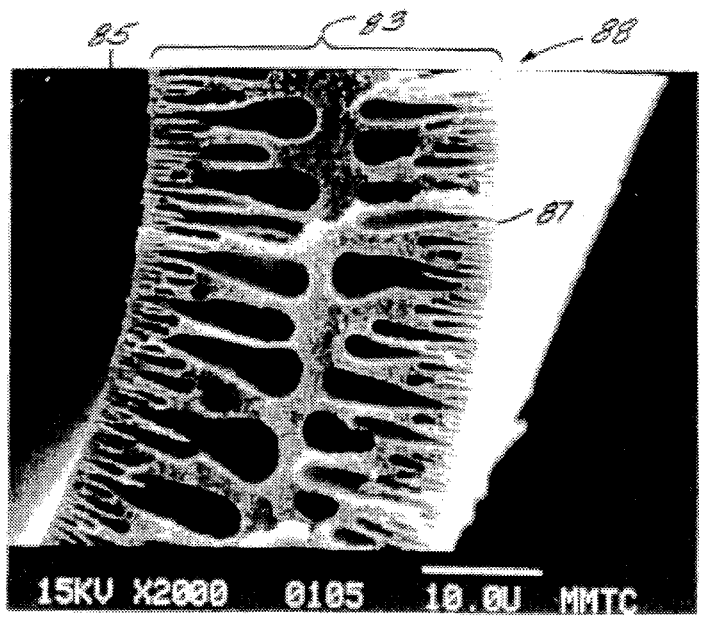
FIGS. 5 and 6 are cross-sectional views of a hollow fiber membrane of the invention of different magnifications taken with an electron microscope.

Referring more specifically to the drawings, FIG. 1 diagrammatically illustrates a hollow fiber spinning system 60. A solution 62 of a polymer in an organic solvent is contained in a vessel 64 from where it is pumped to an annular extrusion die 68 by means of a metering pump 66. Similarly, a coagulant solution 72 which is a non-solvent for the polymer is contained in a second vessel 70 and is transferred to die 68 by means of another pump 74.

The interaction of non-solvent 72 and the polymer solution 62 at the interface 63 formed as the solutions exit the die in contact with each other determine the ultimate structure and properties of the inner membrane.

The formed extrudate then falls through an air gap 76 and enters a bath 78 containing a second non-solvent coagulant solution 80. The interaction of the extrudate with the second solution 80 determines the structure and properties of the outer membrane. The fiber is pulled through the bath 78 by means of a driver roller 82 and through one or more additional baths 84, as required, to completely extract the solvent from hollow fibers. The extracted fiber is finally taken up onto a multisegment winder 86 and allowed to dry. Dried fibers 88 are cut to length and placed in a housing 90. The fibers 88 are sealed in the housing 90 by means of a thermosetting resin 92. The assembly is fitted 30 with end caps 94 and 96. An inlet 97 and an outlet 98 for filtrate liquid are also provided on the housing 90.

Figure 6:
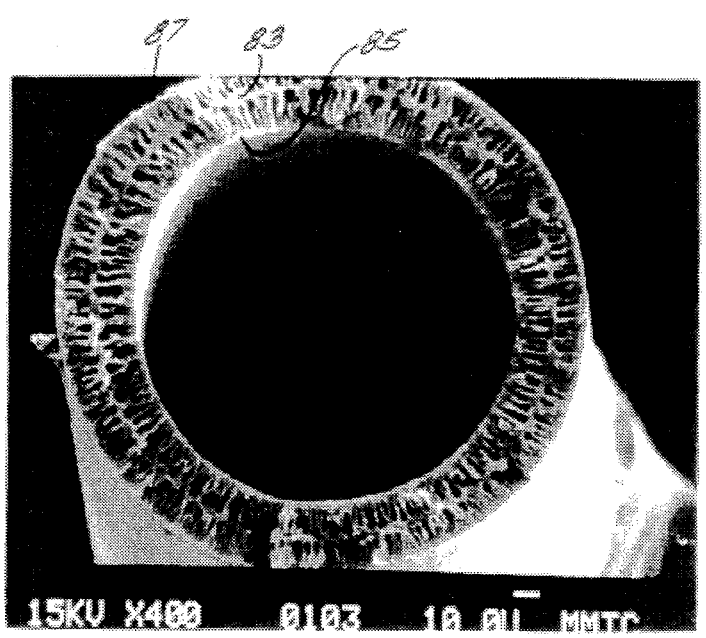

FIGS. 5 and 6 illustrate in magnified cross-section a typical fiber 88 of the invention showing an internal microporous structure 83, an inner skin 85 and an outer skin 87 having different porosity than the inner skin 85. Membranes of this invention preferably have an inner diameter of about 200 microns and generally range in inner diameter from about 100 to 1000 microns.

The overall sieving coefficient is the fraction of the incoming solute that passes through the membrane along with the fluid that is being filtered. It is calculated by dividing the concentration of solute on the downstream side of the membrane by its concentration on the upstream side of the membrane.

For a single-skinned membrane, the overall sieving coefficient is equal to the sieving coefficient of the skin, which is the fraction of solute that passes through that skin. The sieving coefficient of the skin itself depends only on the relative sizes of the pore and the solute molecule. The tighter the skin (i.e. smaller the pores), the smaller the fraction of a given molecule which will pass through it.

However, for a dual-skinned membrane, the concentration of solute which reaches the second skin depends on the characteristics of the first skin as well as the flow conditions, so the overall sieving coefficient is a property of both flow and membrane properties. The key to the rectifying membrane, in which the sieving coefficient in one direction is different from the sieving coefficient in the other direction, is that flow in one direction results in accumulation of solute within the two skins of the membrane.

FIG. 4 is a schematic of a dual-skinned rectifying membrane 88 in which the outer skin 12 is tighter than the inner skin 14 and fluid is passing from the interior to the exterior as a result of an imposed pressure gradient. In this case, some of the molecules which enter the central area 16 of the membrane 88 are unable to leave the central area 16 through the tighter outer skin 12 at the same rate at which they entered through the loose skin 14. As a result of this positive flux, the concentration inside the membrane 88 increases until it reaches a new steady state value at which the net flux of molecules is zero. Concomitant with these changes inside the fiber, the concentration in the fluid 20 outside the fiber increases as well. Since the concentration in the fiber lumen has not changed, the overall sieving coefficient increases with time until it reaches a steady-state value that is higher than would be obtained with the tight skin 12 alone.

If that same membrane 88 is exposed to a pressure gradient from the opposite direction, with flow from the exterior to the interior, the solute first encounters the tight skin 12. The small fraction of the solute which passes through the tight skin 12 can easily pass through the loose skin 14, which means that there is no accumulation within the membrane 88. In this case both the concentration within the membrane 88 and the concentration on the interior 18 are low. The overall sieving coefficient is smaller than that which was obtained in the other direction.

Various polymers can be employed in the process of the invention to form hollow fibers. The polymers must be soluble in at least one organic solvent and insoluble in another liquid that is miscible with the solvent. Examples of suitable polymers are polysulfone, polyetherimide, polyacrylonitrile, polyamide, polyvinylidene diflouride, polypropylene, and polyethersulfone. Illustrative examples of solvents for such polymers include N-methyl-2-pyrrolidone, N,N'-dimethylformamide, N,N'-dimethylacetamide and γ-butyrolactone. The preferred non-solvent which can be used as a coagulation or gelation agent for formation of the skins is water. Other suitable liquids include methanol, ethanol-water mixtures such as 95 or 99.5 vol % ethanol in water, or isopropyl alcohol. Various materials can be added to the non-solvents to form skins of differing porosities. Examples include polyvinyl alcohol, Tetra-ethylene-glycol, poly-ethylene-glycol, perchlorate salts, and polyvinyl pyrrolidone.

An important advantage of the present invention is the ability to provide fibers having different sieving coefficients depending on the direction of filtrate flow, for molecules to be filtered out of a liquid. A further advantage is the ability to provide fibers having different sieving coefficients for filtration out of a liquid of molecules having narrowly defined molecular weight ranges. For example, fibers can be provided that have the ability to filter molecules in the range of 5000 to 10,000 differently from one side of the membrane than the other. By appropriate modification of the porosity, the sieving coefficient differential can also be optimized for molecules having a molecular weight range of 10,000 to 100,000 or even 200,000. Optimization is achieved by adjusting the composition of the coagulant solution and the amount and type of dopants added, as well as by varying the spinning conditions such as flow rate, line speed and gap distance.

EXAMPLES

The following examples illustrate preferred processes for producing and using membranes in accordance with the invention. All parts are given by weight unless otherwise indicated.

EXAMPLE 1

Hollow fibers were prepared using the spinning system and processes described in FIGS. 1 and 2 under the formulation and process conditions shown in Table I.

Test Procedure

Test modules were assembled by potting 100 fibers in mini-dialyzer cases with a length of about 22 cm and an internal diameter of about 0.6 cm. Polyurethane potting extended approximately 1 cm from each header, leaving an active length of about 20 cm. Dialysate ports were located approximately 1 cm from the potting material at each end.

Standard dialysate of the following composition was prepared from concentrate using a hemodialysis machine proportioning system:

| | | |
|---|---|---|
| sodium | 134 | mEq/l |
| potassium | 2.6 | MEq/l |
| calcium | 2.5 | MEq/l |
| magnesium | 1.5 | MEq/l |
| chloride | 104 | MEq/l |
| acetate | 36.6 | MEq/l |
| dextrose | 2500 | MEq/l |

Myoglobin solution was prepared by adding 330 mg of myoglobin per liter of dialysate. Myoglobin (molecular weight= 17,000) is used as a marker for middle molecules such as B-2 microglobuylin (molecular weight= 12,000) because it can be measured spectrophotometrically.

The lumen and filtrate compartments were primed with alcohol (isopropanol or ethanol) using a syringe. The test module was then rinsed with excess dialysate, pumping 250 ml through the lumen with the filtrate port closed and then 200 ml more with one filtrate port open. To measure inlet flow rate, the dialysate ports were closed, the infusion pump was set to the desired speed (10.5 ml/min), and outflow was determined by timed collection.

For the sieving coefficient measurement, the test module was clamped in a vertical position with fibers perpendicular to the table top. An infusion pump was connected to an inlet reservoir, and tubing from the infusion pump was connected to the bottom header. Tubing to waste was connected to the top header. The dialysate ports were closed, the pump was started, and the time at which the test solution reached the device was denoted as time zero.

At time zero, the dialysate side was drained of priming solution by opening both dialysate stopcocks. The lower dialysate port was then closed, and the time zero filtrate sample was taken from the upper port as soon as the filtrate compartment was filled. At the same time, the outlet lumen sample was collected into another beaker. Inlet lumen samples were taken directly from the inlet reservoir. Subsequent filtrate samples were collected at 3 minute intervals, with no loss of filtrate between samples. All samples were measured for myoglobin content using a Gilford spectrophotometer. The sieving coefficient, S, was calculated using the following equation:

$$S = \frac{2 \times \text{concentration dialysate}}{(\text{inlet lumen concentration} + \text{outlet lumen concentration})}$$

Sampling was continued until the calculated sieving coefficient was constant for three consecutive samples. The fibers were assembled into test modules and the sieving coefficients determined in accordance with the foregoing procedure. The sieving coefficients of the fibers of this example for myoglobin were found to be 0.35 when filtrate flow was directed radially outwardly and 0.80 when filtrate flow was inward.

| | |
|---|---|
| Polymer | Polysulfone |
| Solvent | N-methylpyrrolidone |
| Spinning Solution Concentration | 15 g/100 g |
| Core Fluid Composition | 15/85 2-propanol/water |
| Precipitation Bath Composition | 2/98 2-propanol/water |
| Wash Baths Composition | Water |
| Gap Distance | 1 cm |
| Line Speed | 18 meters/min |
| Spinning Solution Flow Rate | 1.8 cc/min |
| Core Fluid Pin Diameter | 0.009 inches |
| Die Annular Gap | 0.0035 inches |

EXAMPLE 2

Hollow fibers were prepared as in Example 1 except that the core fluid composition was 10/90 2-propanol/water and that of the precipitation bath was 5/95 2-propanol/water. FIGS. 5 and 6 are scanning electron micrographs of the resulting fiber in cross-section taken at 2000 times magnification and 400 times magnification, respectively, showing the finger-like structures extending from each boundary and meeting in the middle wall. Sieving coefficients for myoglobin were found to be 0.45 for outward filtrate and 0.90 for inward flow.

EXAMPLE 3

Hollow fibers were prepared as in Example 1 except that the core fluid composition was 70% isopropyl alcohol and 30% water. The spinning solution concentration was 20 weight percent of polysulfone in N-methylpyrrolidone with 10% acetone. The precipitation bath was water. Sieving coefficients were determined for dextran using the following procedure:

1) Dextran Sieving Coefficient. A dextran solution of the following composition was prepared in phosphate buffered saline (0.9%):

Dextran FP1 (Serva) 0.2 g/l

Dextran 4 (Serva) 1.0 g/l

Dextran T40 (Pharmacia) 1.0 g/l

Dextran T10 (Pharmacia) 0.3 g/l

Dextran solution was perfused through the lumen with filtrate collected from the shell side. Dextran solution was also perfused through the shell side with filtrate collected from the lumen. The order of the tests varied. Solution flow rate was 5 ml/min, and the transmembrane pressure was between 150 and 200 mm Hg. Inlet samples were taken directly from the dextran solution reservoir. Filtrate samples were taken at five minutes intervals. The filtrate concentration values stabilized after fifteen minutes. The filtrate concentration value at forty or sixty minutes were used to calculate sieving coefficient. The bulk solution concentration was assumed to be equal to its inlet value and constant throughout the length of the dialyzer. Samples were analyzed by high performance liquid chromatography (HPLC) using a refractive index detector.

$$S = \frac{\text{filtrate concentration}}{\text{bulk concentration}}$$

Figure 8:
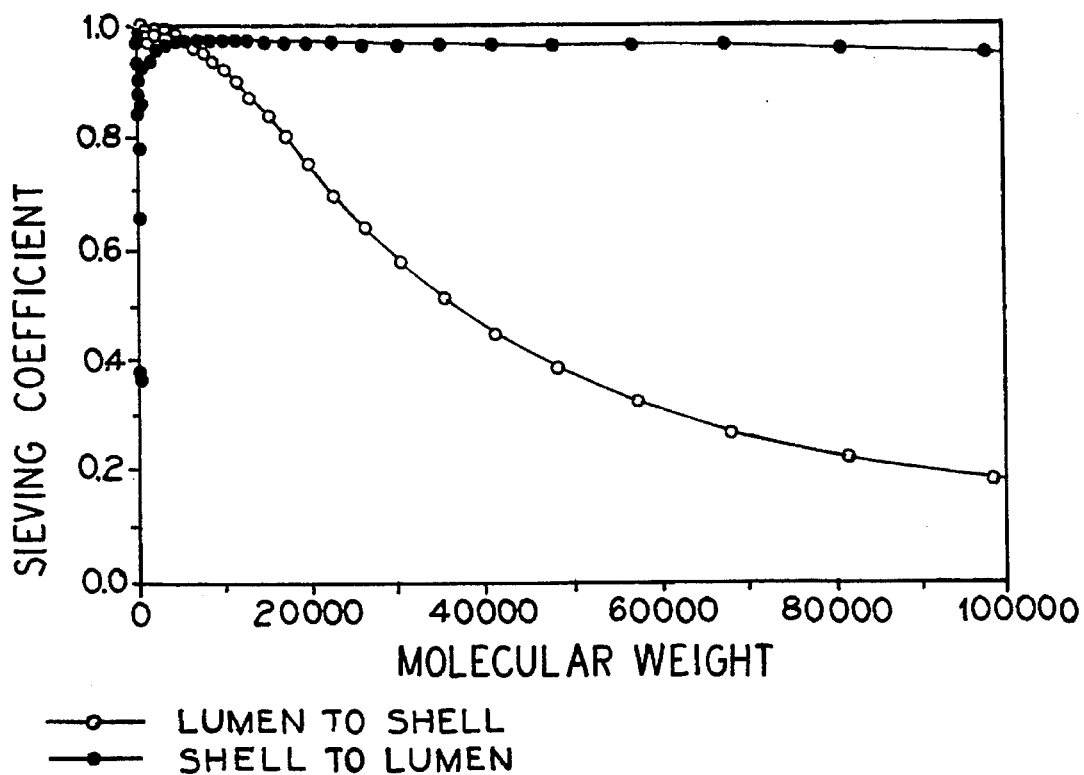
FIGS. 8–14 are graphical representations of the results obtained from testing of specific examples described herein.

Results are shown in FIG. 8.

Sieving coefficients for alcohol dehydrogenase (MW approximately 150,000) and β-amylase (MW approximately 200,000) were determined by the procedure outlined above, by with the samples analyzed by a commercially available assay kit (Sigma Chemical Co.). The sieving coefficients for alcohol dehydrogenase were 0.05 for outward flow and 0.76 for inward flow. The sieving coefficients for β-amylase were 0.01 for outward flow and 0.17 for inward flow.

EXAMPLE 4

Figure 9:
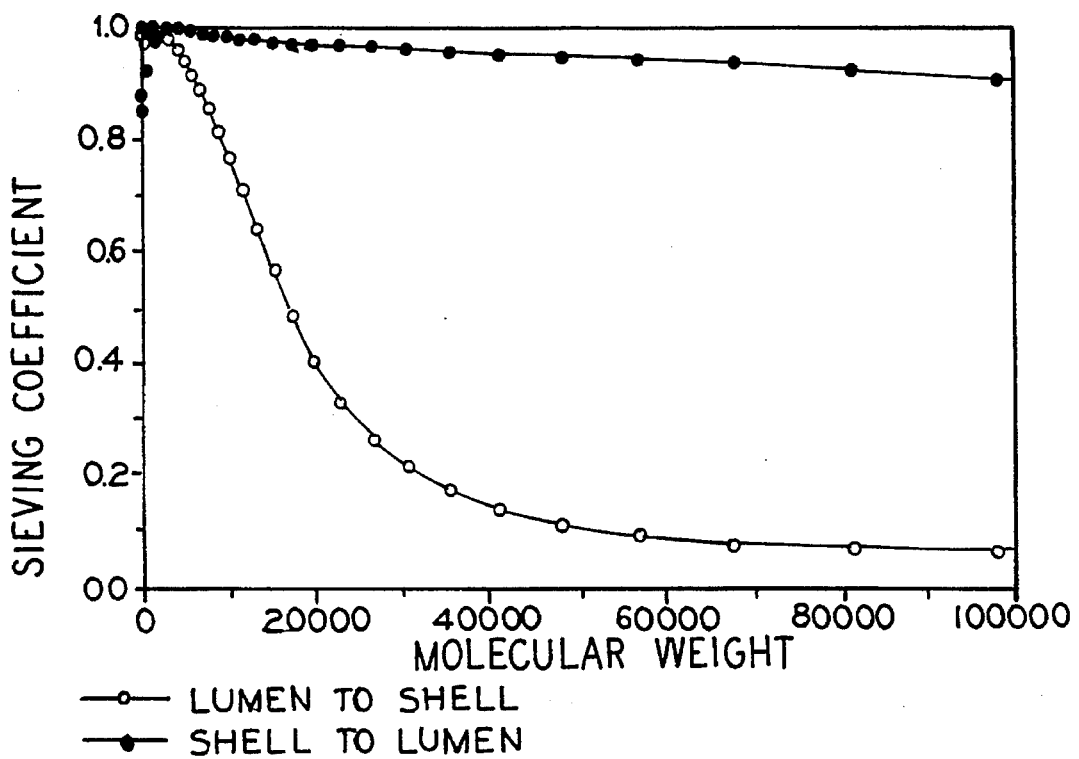

Hollow fibers were prepared as in Example 1 except that the core fluid composition was 50% isopropyl alcohol and 50% water. The spinning solution contained 20% by weight of polysulfone and N-methylpyrrolidone with 10% acetone. The precipitation bath was water. The sieving coefficient for dextran was determined for lumen to shell and shell to lumen. The results are shown in FIG. 9.

EXAMPLE 5

Figure 10:
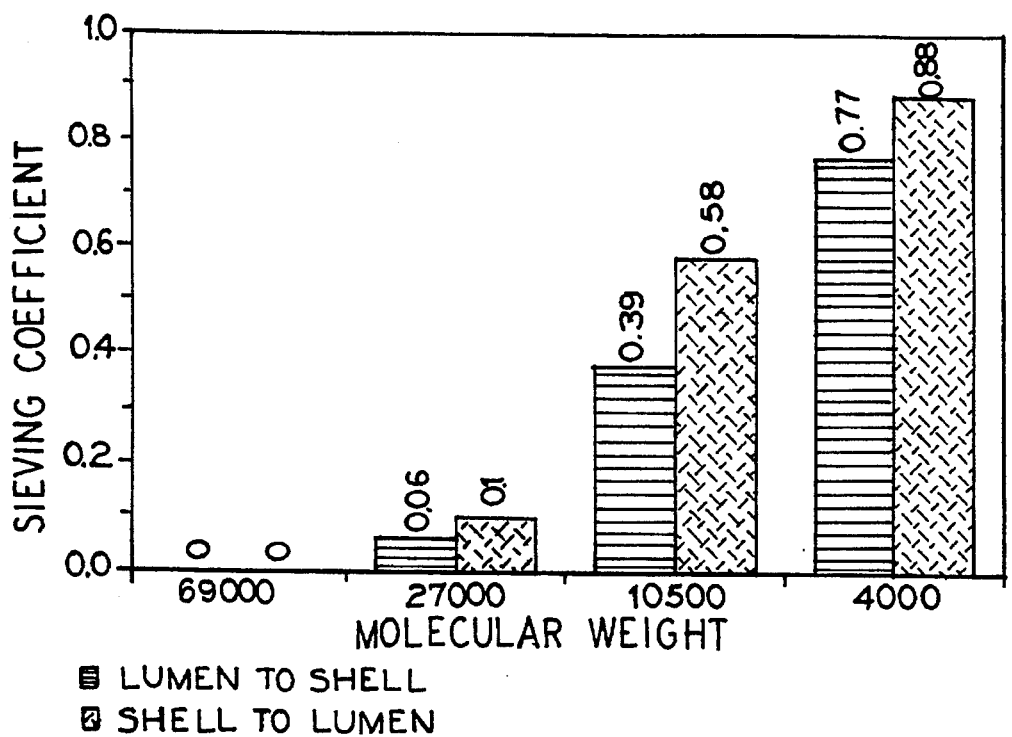

Hollow fibers were prepared as in Example 1 except that the core fluid composition was isopropyl alcohol. The spinning solution was polysulfone in a concentration of 15% by weight and in addition 15% by weight of polyvinylpyrrolidone in N-methylpyrrolidone. The core fluid composition was isopropyl alcohol, and the precipitation bath was water. The sieving coefficient for dextran was determined as in Example 3 with the results being shown in FIG. 10.

EXAMPLE 6

Polysulfone hollow fiber membranes were prepared with an outer skin having a 5,000 kilodalton (kD) nominal molecular weight (MW) cutoff and a skin with a larger, but unknown MW cutoff on the inner fiber surface. For these fibers, the sieving coefficients of dextrans of various molecular weight were found to be greater when filtrate flow was directed radially inward than when filtrate flow was directed outward.

Protein Sieving Coefficient. The following proteins were dissolved in phosphate buffered saline (0.9%):

| | |
|---|---|
| Solution 1 | 2.0 g/l |
| Bovine serum albumin | |
| Solution 2 | 1.0 g/l |
| Ovalbumin (chicken egg albumin) | |
| Solution 3 | 0.08 g/l |
| Myoglobin | |
| Solution 4 | 0.12 9/1 |
| Cytochrome c | |

Protein solution was perfused through the lumen with filtrate collected from the shell side. Protein solution was also perfused through the shell side with filtrate collected from the lumen. The order of the tests varied. Inlet samples were taken directly from the protein solution reservoir. Filtrate samples were taken at five minute intervals. The filtrate concentration values stabilized after fifteen minutes. The filtrate concentration value at forty or sixty minutes were used to calculate sieving coefficient. The bulk solution concentration was assumed to be equal to its inlet value and constant throughout the length of the dialyzer. Samples were analyzed for absorbance at a characteristic wavelength using a spectrophotometer. Bovine serum albumin and ovalbumin were analyzed at 280 nm. Myoglobin and cytochrome c were analyzed at 410 nm.

Figure 11:
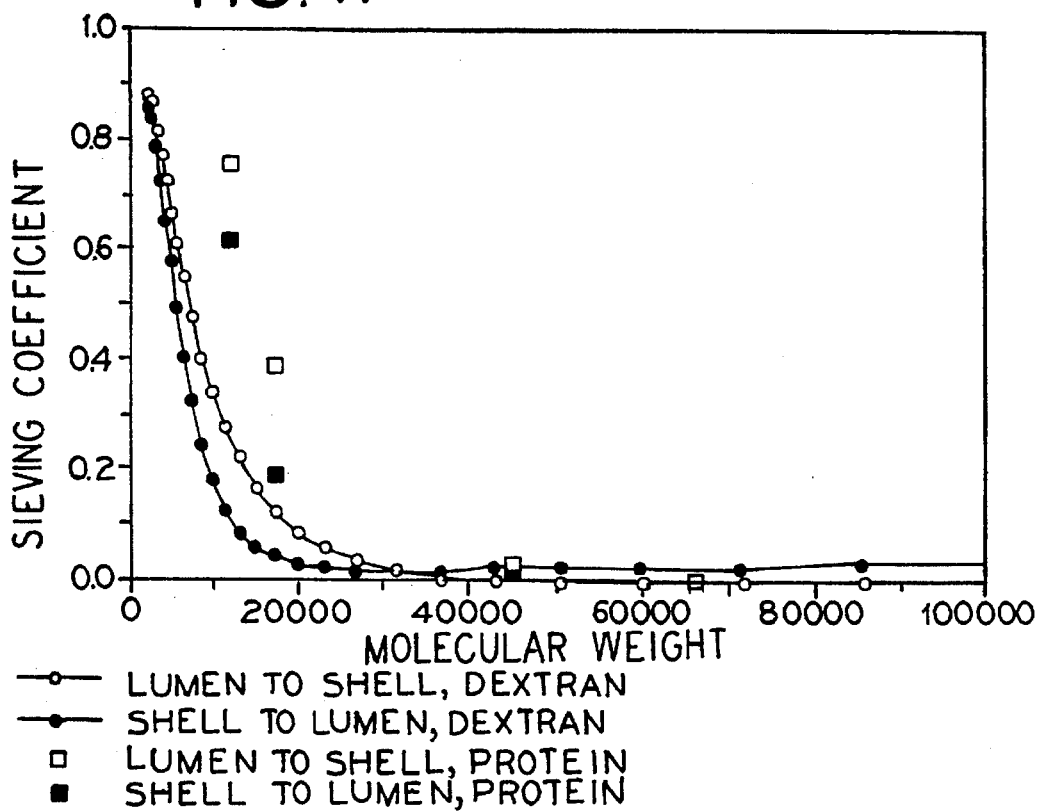

The results for sieving coefficients of both dextran and proteins tested according to the foregoing procedure are shown in FIG. 11.

EXAMPLE 7

Hollow fibers were prepared according to the procedure of Example 1 using the following materials:

Polymer: Polyetherimide

Solvent: N-methylpyrrolidone

Spinning solution concentration: 20 wt %

Core fluid composition: Water

Precipitation bath: Water

Figure 12:
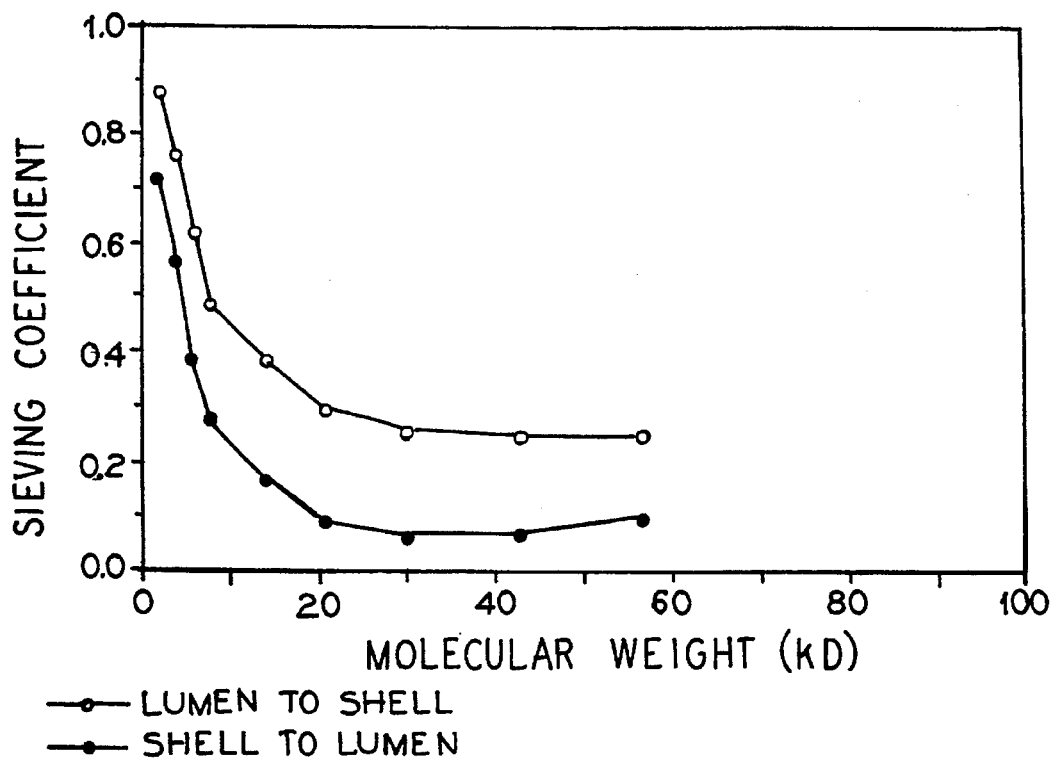

The sieving coefficient data for dextran when tested is shown in FIG. 12.

EXAMPLE 8

Hollow fibers were prepared according to the procedure of Example 1 using the following materials:

Polymer: Polyetherimide

Solvent: N-methylpyrrolidone

Spinning solution concentration: 25 wt

Core fluid composition: 50/50

Water/N-methylpyrrolidone

Precipitation bath: Water

Figure 13:
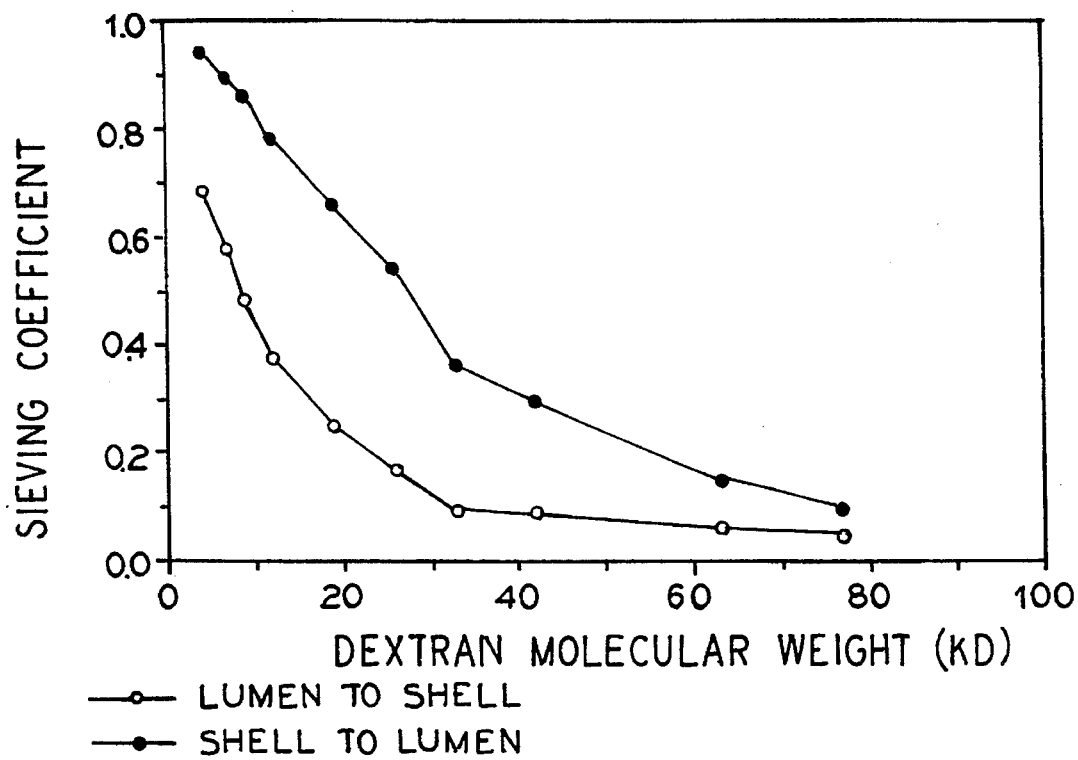

The sieving coefficient data for dextran is shown in the following FIG. 13.

EXAMPLE 9

Figure 14:
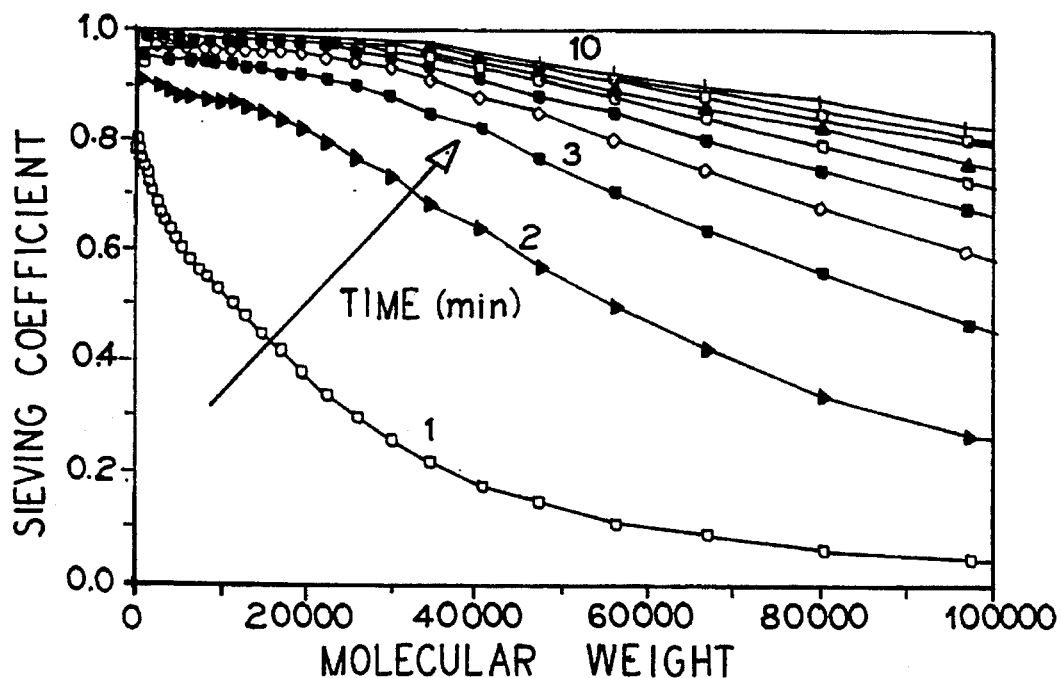

According to current theory on the behavior of rectifying membranes, internal concentration polarization of solute is responsible for the asymmetric sieving characteristics of the above 35 examples. The accumulation of solute between the two skins of the membrane should require a finite amount of time to occur. Consequently, the sieving coefficient in one direction should increase with time until equilibrium is reached. For most common membranes, the sieving coefficient is generally greatest in early time measurements and may decrease with time as pores clog with retained solute. In FIG. 14, the sieving coefficient in the shell to lumen direction is shown as a function of time for the membrane of Example 3. For this experiment, filtrate was collected at one minute intervals for the first ten minutes of filtration. The sieving coefficient, particularly in the 50,000 to 100,000 range, did increase significantly with time.

Figure 7:
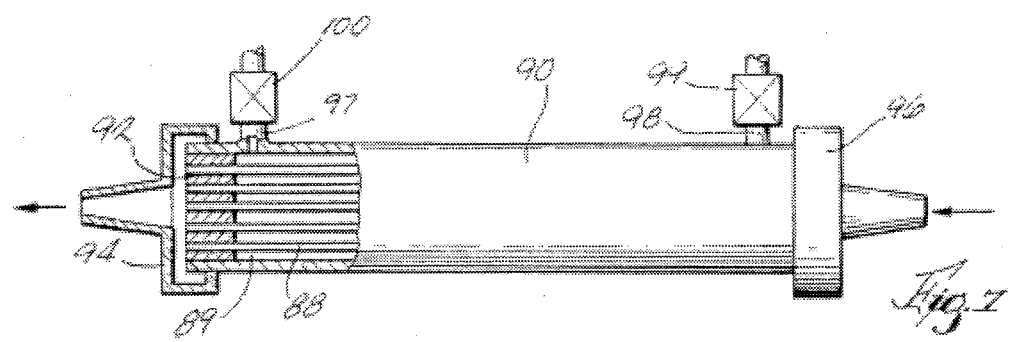
FIG. 7 is a side elevational view of a bioreactor device in accordance with the invention.

A bioreactor is shown in FIG. 7 and consists of a device somewhat similar to the dialysis device shown in FIG. 3. In this case, however, a space 89 surrounding the fibers and enclosed by the interior of a housing 90 and a thermosetting resin 92 forms a reaction vessel for growth of living cells. Ports 97 and 98 are either omitted or can be closed by means of valves 99 and 100 as indicated. Depending on its size, the product may pass back through the membranes 88 and be purified from the waste stream or it may collect in the shell space which constitutes the reaction vessel from which it may be removed on either a semi-continuous or batch basis.

Transport of nutrients, waste products and desired biological products across the membrane may be by diffusion and/or convection. The axial pressure drop which occurs within the hollow fibers leads to Starling's flow with convection from the tube side to the shell side at the device inlet and with convection from the shell side to the tube side at the device outlet.

Some types of cells require expensive growth media which may contain 10% bovine fetal calf serum. Use of a rectifying membrane allows serum components to pass through the membranes to the cells and then be concentrated in the shell space, thereby reducing the volume of media required. This also reduces the cost of purifying products which pass through the membrane because the volume of the purification stream is smaller.

Rectifying membranes can also be used to concentrate products directly. If the desired product is formed of molecules that are larger than the metabolic waste products as well as the nutrients, the rectifying membrane device can be used to concentrate the products in the shell space while allowing nutrients to reach the cells and waste products to be washed away by the fluid stream passing through the interiors of the hollow fiber membranes.

Membranes in accordance with the present invention can thus be formed with the tighter skin either on the interior or exterior of a hollow membrane. In either event, it is important that the skins on each side of the membrane contain pores that are invisible at 10,000 times magnification. This will insure the presence of sufficiently tight skins on each side of the membrane to cause a build up of solutes in the microporous interior of the membrane between the skins. Such build-up of solutes is believed to be important to the construction of membranes in which different sieving coefficients are obtained for flow through the membrane in different directions.

In a further application of the membrane, solute concentration may be effected in the filtrate. As previously described with reference to FIG. 4, the dual-skinned rectifying membrane 88 has an outer skin 12 which is tighter than the inner skin 14. Fluid passes from the inside to the outside as a result of an imposed pressure gradient. The membrane 88 as described exhibits asymmetric sieving characteristics. That is, the sieving coefficient for the membrane 88 in one direction is generally substantially different than sieving coefficients in the other direction. Thus, the fraction of solute that passes through the membrane 88 in one direction is different than that fraction of the solute that passes through the membrane in the other direction.

By repeatedly cycling solution back and forth across the membrane 88, the solute can be separated and concentrated on one side of the membrane 88. Beginning with a concentrated solution on the shell side of the membrane 88 wherein the membrane 88 has a greater sieving coefficient in the shell to lumen direction, solute can be concentrated on the lumen side of the membrane 88 by the repeated cycling of the solution back and forth across the membrane 88.

This concept can be used for a variety of applications. Such applications include dialysis and bioreactors.

EXAMPLE 10

100 ml of 0.2% bovine serum albumin (BSA) was placed in a reservoir on the shell side of a rectifying membrane. Fluid was recirculated on the shell side of the membrane at a rate of 300 ml per minute. The filtration rate was approximately 1 ml per minute. In the first pass, 60 ml was filtered into a reservoir on the lumen side. Then, approximately 40 ml was cycled back and forth between the two reservoirs. After five cycles, 25 ml of solution on the lumen side contained BSA at a concentration equal to 2.8 times its original value on the shell side.

Figure 15:
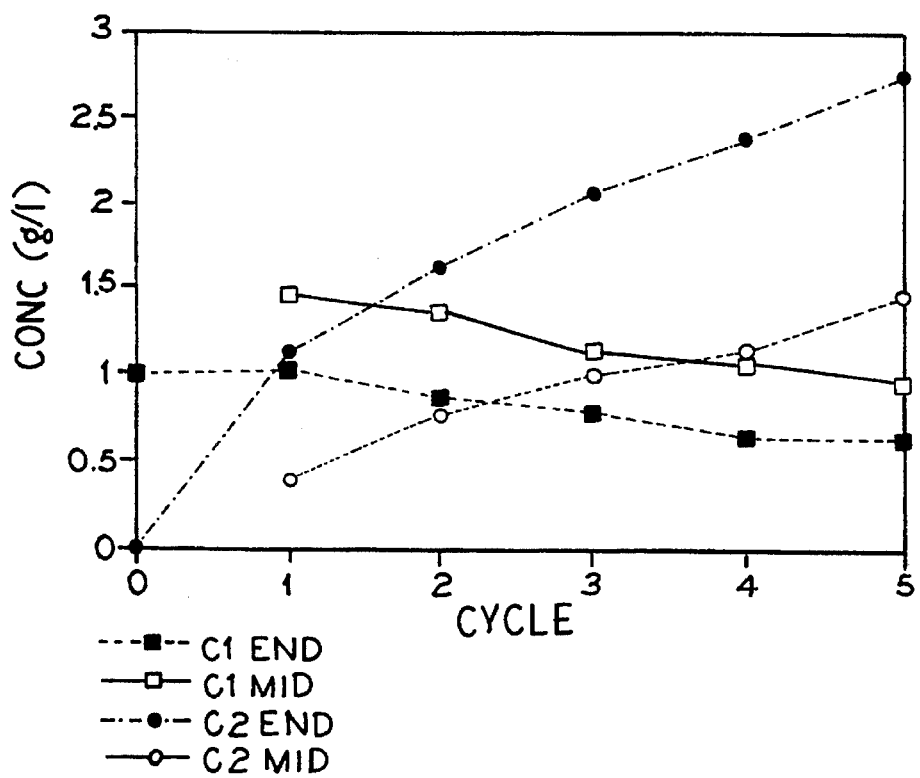
FIG. 15 is a graphical representation of the results obtained from oscillating the filtration device and the resultant solute concentration.

FIG. 15 graphically illustrates the concentration in grams per liter of BSA on each side of the device at the middle of each cycle and at the end of each cycle. As is apparent, in the first half of each cycle, the concentration in side one (C1MID) is relatively high while the concentration in side two (C2MID) is relatively low. In the second half of the cycle, the concentration in side one (C1END) decreases as it is diluted by solution returning from side two. The final downstream concentration (C2END) is shown to substantially increase with each progressive cycle.

Figure 16:
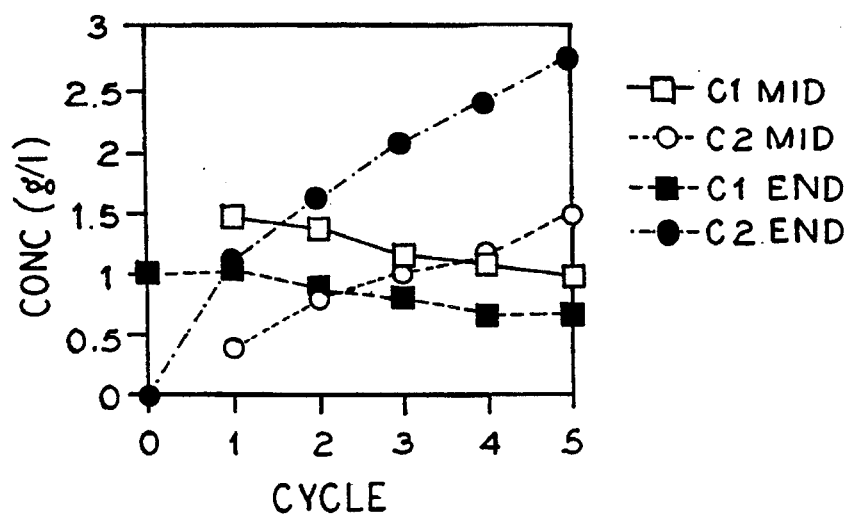
FIGS. 16–20 are graphical representations of the results obtained from oscillating the filtration device with a range of sieving coefficients and the resultant solute concentrations.
Figure 17:
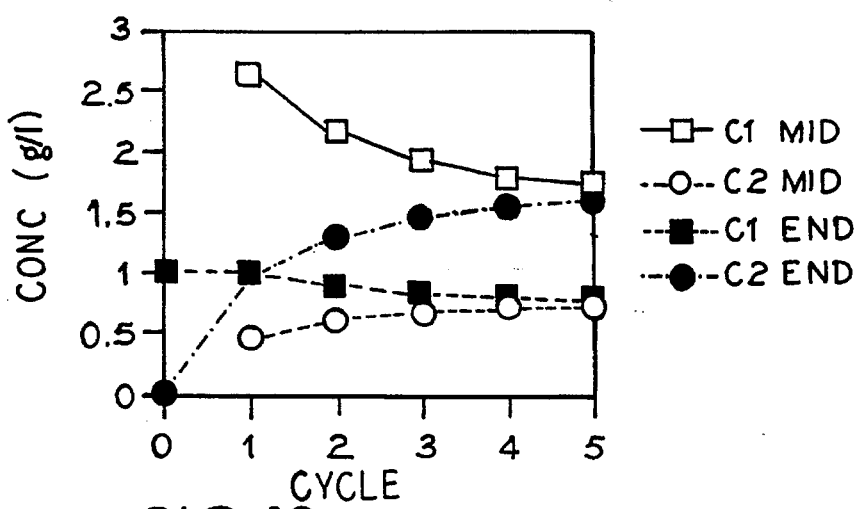
Figure 18:
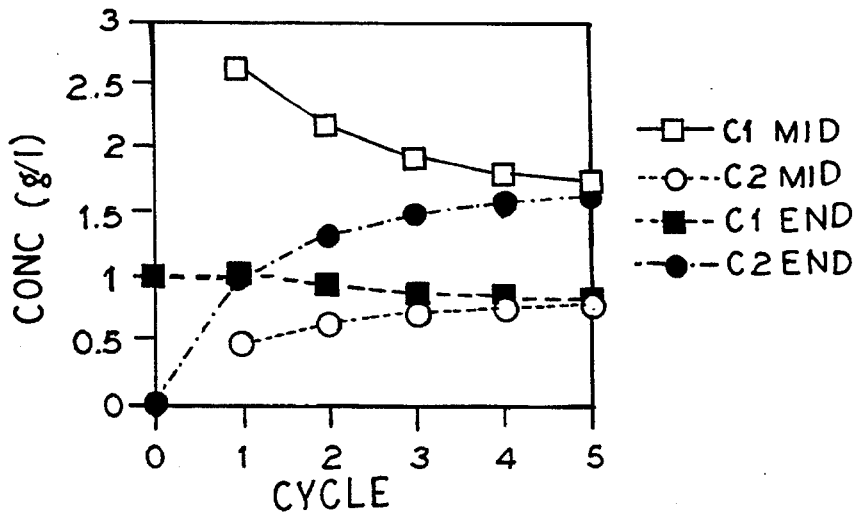
Figure 19:
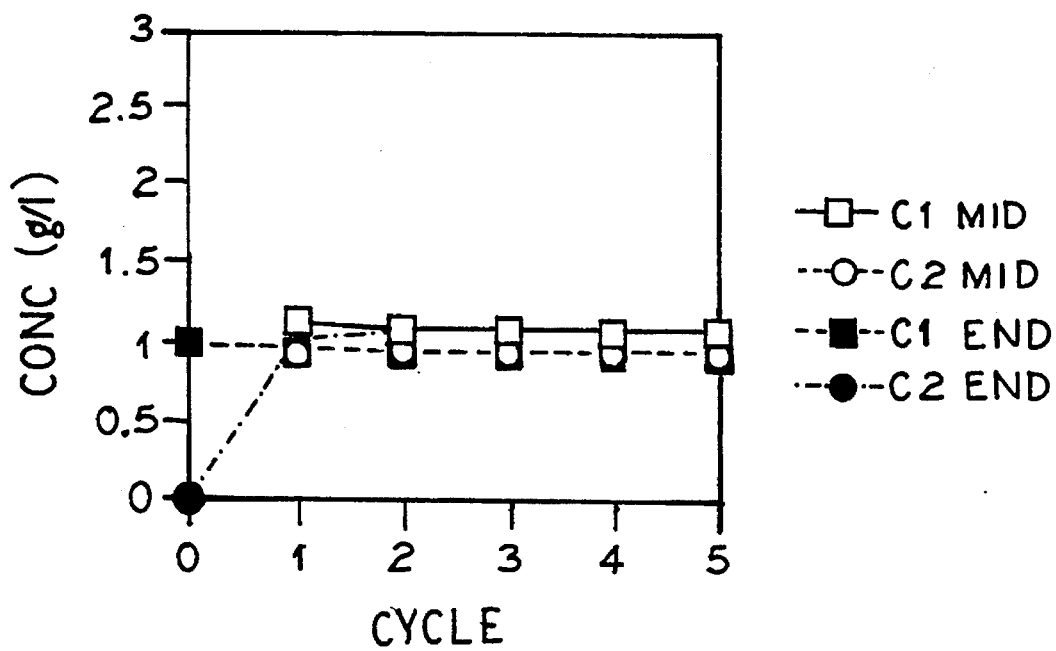
Figure 20:
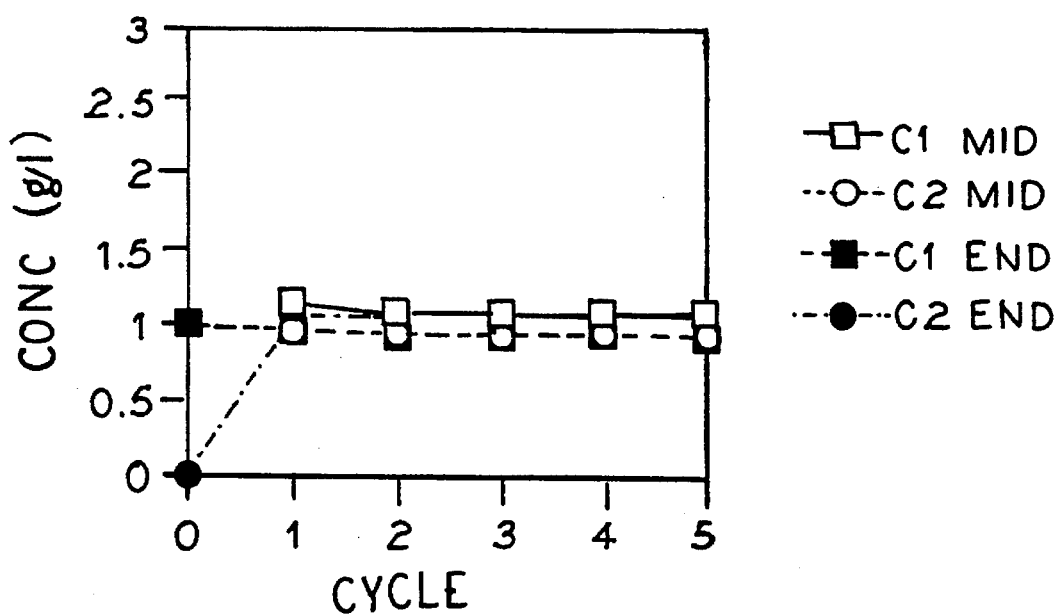

FIGS. 16–20 graphically illustrate computer simulations of simple single skinned membranes varying concentration at the middle and the end of each cycle for varying sieving coefficients of the membrane. In FIG. 16, the sieving coefficient equals 0.1; in FIG. 17, the sieving coefficient equals 0.3; in FIG. 18, the sieving coefficient equals 0.5; in FIG. 19, the sieving coefficient equals 0.7; and in FIG. 20, the sieving coefficient equals 0.9.

As is apparent from FIGS. 16–20, the dual-skinned rectifying membrane 88 shows a continual increase in solute concentration on side two. Most single skin membranes, however, equilibrate within a few cycles. As shown in FIGS. 16–20, the greatest downstream concentration to be attained was 1.62 which corresponds to a single skinned membrane having a sieving coefficient equal to 0.3.

From the foregoing, one can see that use of a dual-skinned rectifying membrane 88 results in a downstream concentration of 2.8 times the initial concentration after five experimental cycles. This is 70% higher than that of any single skin membrane. Of course, even higher concentrations are possible depending on the particular solute membrane interactions and the operating conditions of the device.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A method for removing unwanted material from a solution comprising the steps of:

providing a device having a plurality of dual-skinned hollow membranes secured in a generally parallel orientation in an enclosure wherein a first, skin of the dual-skinned membrane has a different degree of porosity than its second skin providing an asymmetric sieving coefficient with respect to passage of a solution including solute to be removed through the membrane;

causing the solution to flow through the device a plurality of times in an oscillating manner; and removing the solute by accumulating the solute on at least a first side of the membranes as the solution is transferred through the device.

2. The method of claim 1 wherein the sieving coefficient is between 0.1 and 0.9 inclusive.

3. The method of claim 1 wherein the solution is a dialysis fluid.

4. The method of claim 1 further comprising the steps of:

providing a first reservoir on one side of the membrane; and providing a second reservoir on a second side of the membrane wherein the solution is caused to flow between the first reservoir and the second reservoir through the device.

5. The method of claim 1 further comprising the step of:

providing an inflow means in fluid communication with interiors of the membranes.

6. The method of claim 1 further comprising the step of:

providing an outflow means in fluid communication with ends of the membranes for outflow of the solution.

7. The method of claim 1 further comprising the step of:

providing a second fluid flow path in fluid communication with an interior of the enclosure wherein the solution can be caused to flow in contact with exterior surfaces of the membranes.

8. The method of claim 1 wherein the solute has molecular weights within a defined range.

9. A method of removing unwanted material from a bodily fluid comprising the steps of:

providing a dialysis device having a plurality of dual-skinned polymeric membranes wherein a first skin of the dual-skinned membrane has a different degree of porosity than its second skin, each membrane having a shell side and a lumen side and each membrane secured at opposite ends in a generally parallel orientation within an enclosure;

providing an inflow means for a liquid subjected to dialysis, the inflow means for a liquid subjected to dialysis, the inflow means in fluid communication with the lumen sides of the membranes;

providing an outflow means in fluid communication with ends of the membrane for outflow of the bodily fluid after filtration; and causing the bodily fluid to flow through the device a plurality of times wherein at least some of the unwanted material collects in the shell sides of the membranes.

10. The method of claim 9 wherein the plurality of membranes have a microporous structure.

11. The method of claim 9 wherein the plurality of membranes have a microporous structure providing an asymmetric sieving coefficient.

12. The method of claim 11 wherein the microporous structure providing an asymmetric sieving characteristic is greater for flow from interior to exterior than from exterior to interior.

13. The method of claim 9 wherein the unwanted material is of a defined range of molecular weights.

14. The method of claim 9 wherein the bodily fluid is human blood.

15. The method of claim 9 wherein the unwanted material removed from the bodily fluid is $\beta$-2-microglobulin or other middle molecules.

16. A method of producing biological products by confining living cells in a bioreactor vessel, the vessel having a plurality of dual-skinned hollow membranes with a microporous structure having an asymmetric sieving coefficient wherein the first skin of the dual-skinned membrane has a different degree of porosity than its second skin, the membranes secured in a generally parallel orientation in an enclosure having an interior wherein exteriors of the membranes and the interior of the enclosure define the bioreactor vessel, the method comprising the steps of:

causing a fluid containing nutrients for the cells to repeatedly flow through the hollow membranes in cycles to allow transport of the nutrients through the membrane to the cells; and removing waste materials from the cells as the waste materials are transferred through the membranes to the fluid.

17. The method of claim 16 including the step of:

removing a biological product from the vessel.

\* \* \* \* \*